United States Patent [19]

Prenovitz et al.

[11] Patent Number: 4,611,888

[45] Date of Patent: Sep. 16, 1986

[54] COUPLER FOR SURGICAL ENDOSCOPE AND VIDEO CAMERA

[75] Inventors: Melvin B. Prenovitz; Koichiro Hori, both of Framingham, Mass.

[73] Assignee: MP Video, Inc., Natick, Mass.

[21] Appl. No.: 542,742

[22] Filed: Oct. 17, 1983

[51] Int. Cl.⁴ .................................................. G02B 6/40
[52] U.S. Cl. ...................................... 350/96.22; 126/6; 350/96.26
[58] Field of Search .............................. 128/6, 303.1; 350/96.20, 96.22, 96.24–96.27

[56] References Cited

U.S. PATENT DOCUMENTS

| | | | |
|---|---|---|---|
| 3,503,386 | 3/1970 | Pieratt | 128/276 X |
| 4,027,938 | 6/1977 | Lewis | 350/96.22 |
| 4,312,563 | 1/1982 | Mead | 350/96.20 |
| 4,330,169 | 5/1982 | Kantor | 350/96.26 X |

Primary Examiner—William L. Sikes
Assistant Examiner—Lester Rushin
Attorney, Agent, or Firm—Wolf, Greenfield & Sacks

[57] ABSTRACT

A device for coupling a rigid surgical endoscope and a video camera has a compact, lightweight configuration which receives the endoscope without the conventional bulky endoscope eyepiece. The coupler has front and rear sections rotatable with respect to each other under a frictional drag to enable the endoscope and camera to be rotated either in unison or with respect to each other, so as to change the field of view of the endoscope or to change the orientation of the image on the screen of a video monitor, or both. The device includes sealing means to prevent fogging of the optics while enabling complete immersion of the endoscope, coupler and video camera, as a unit, in suitable liquid sterilization bath. The coupler also is adapted to accept endoscopes of various configurations.

18 Claims, 6 Drawing Figures

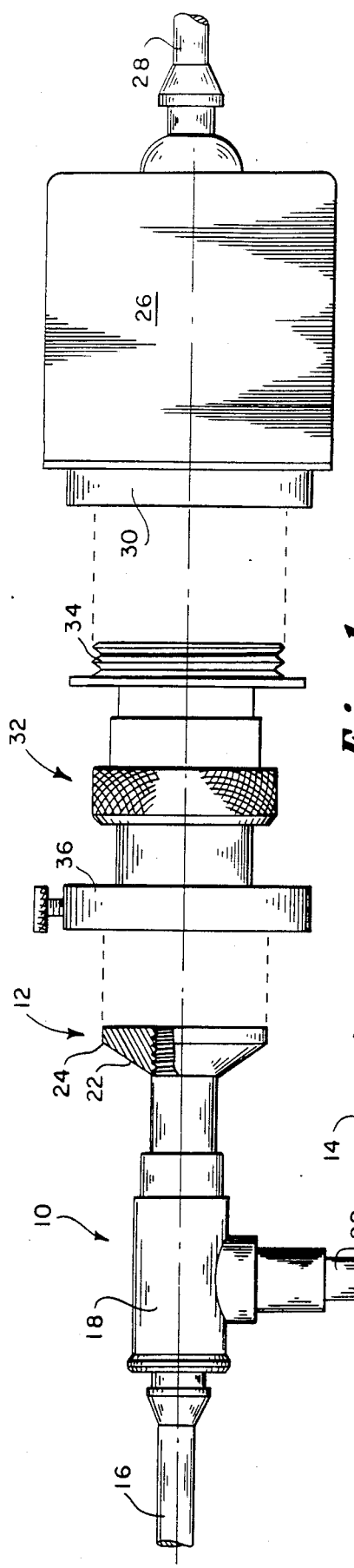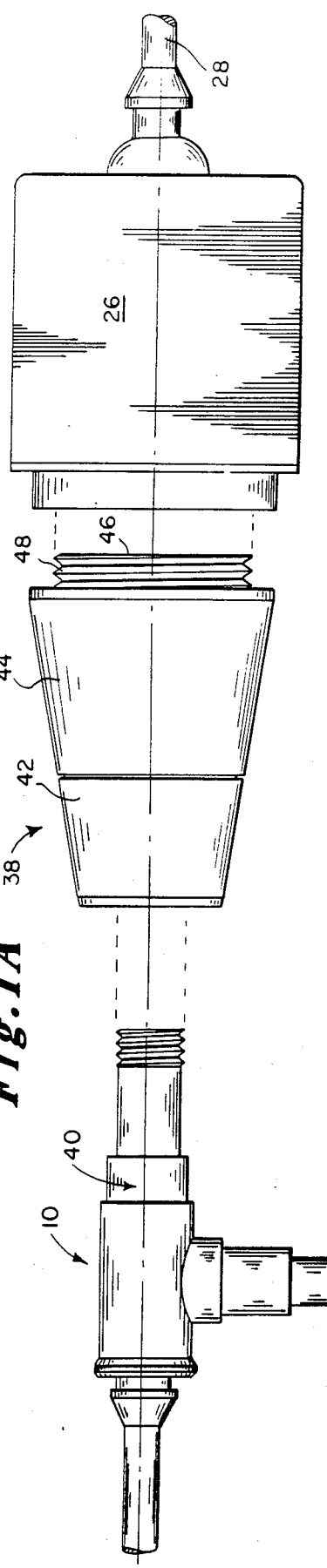

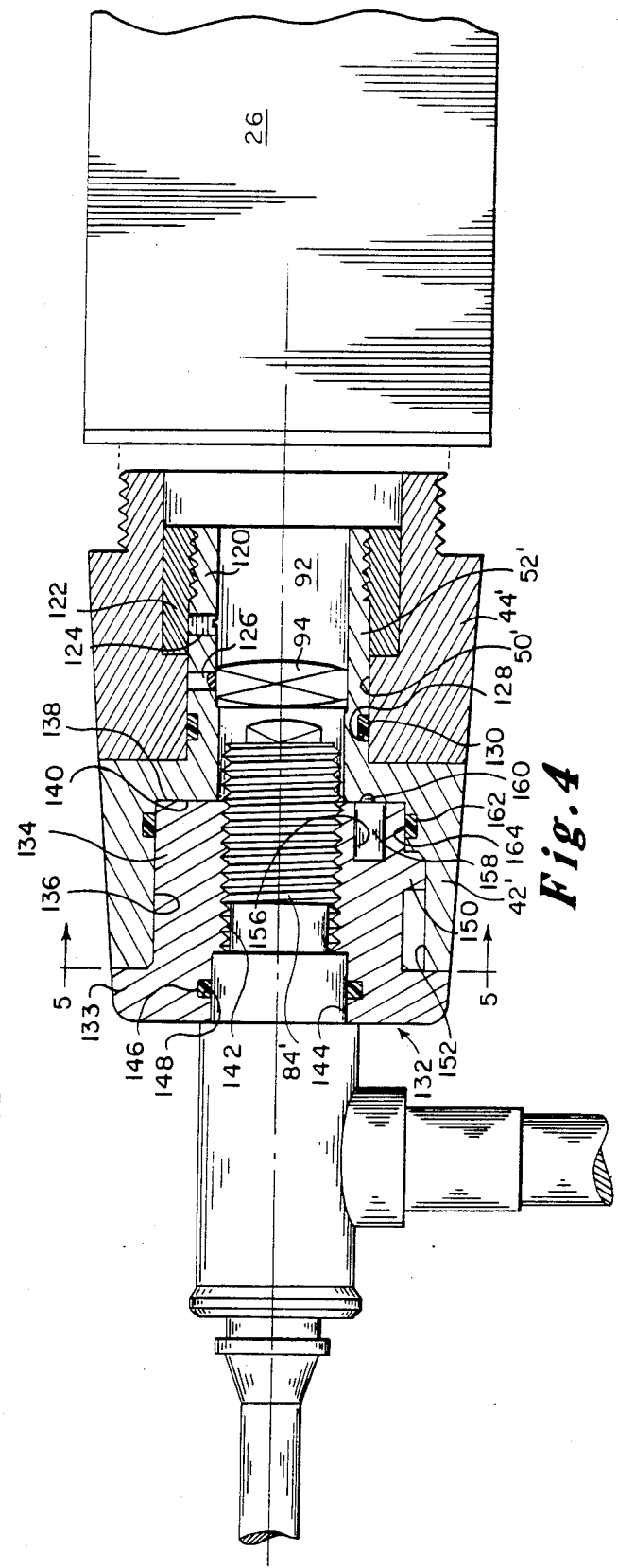
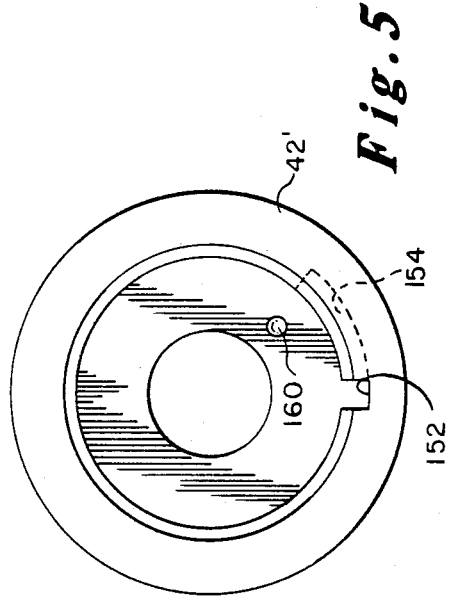
Fig.4
Fig.5

COUPLER FOR SURGICAL ENDOSCOPE AND VIDEO CAMERA

THE FIELD OF THE INVENTION

This invention relates to improvements in devices used in video endoscopy and, particularly, to a coupling device to connect a rigid surgical endoscope to the video camera.

BACKGROUND OF THE INVENTION

In recent years the use of endoscopic surgical procedures has increased. Endoscopic surgical techniques have enabled the simplification of many surgical procedures which previously required extensive surgery with its attendant risks and problems. Often operations which ordinarily might take many hours and extensive recuperation periods may be reduced to relatively short duration with only brief recuperation required. For example only, endoscopic surgical procedures are used widely in diagnosis and surgical treatment for joint ailments, such as knee surgery.

In an endoscopic surgical procedure a small incision is made through which a rigid endoscope is inserted. The endoscope includes an optical system having an objective lens at its distal end and viewing optics at its proximal end so that the surgeon may inspect visually that part of the body into which the endoscope has been inserted. Light for illumination of the region to be viewed is transmitted through optical fibers which extend through the endoscope to its distal end. The proximal end of the endoscope typically is provided with an eyepiece to facilitate handling and viewing by the surgeon. The endoscope may be used to make a diagnostic inspection as well as during a corrective surgical procedure. When used in a corrective procedure the surgery is performed by making another small incision nearby through which a guide tube is inserted. Miniature surgical instruments then are passed through the guide to the internal surgical field. The surgeon manipulates the miniaturized instruments while simultaneously viewing through the endoscope the surgical field within the patient's body Direct viewing through the eyepiece of the endoscope typically requires that the surgeon must bend over for extended periods of time with great strain and fatigue both to eyes and back. In an effort to overcome this fatiguing effect it has become increasingly common to connect a video camera to the eyepiece of the endoscope and to observe the surgical field on a video monitor connected to the video camera. Thus the surgical procedure may be seen magnified substantially on a video monitor, the surgeon can perform the surgery comfortably with less fatigue, and the surgery can proceed faster and more efficiently.

In order to connect the endoscope to the video camera an intermediate coupling device is used. Typically the coupling device has a fitting at its rear end which attaches to the video camera. The front end of the coupler typically has a coupling ring which receives and grips the endoscope by the eyepiece. The couplers typically have intermediate lenses which focus the image from the endoscope optics on the focal plane of the camera. The coupling ring engages the endoscope eyepiece in a manner which enables the endoscope to be rotated, by its eyepiece, in the coupling ring. That enables the endoscope and camera to be rotated relative to each other, either to reorient the image on the video monitor or to redirect the field of view within the patient's body. Typically the coupling devices also enable the endoscope to be detached from the coupling so that endoscopes may be changed. In that regard, it is not uncommon for some procedures to require the use of a number of endoscopes, each having special optical or structural characteristics for different purposes. Sometimes fogging of the optics requires a change in endoscopes so as to maintain optical clarity during the procedure.

While the foregoing devices used in video endoscopy have been significant advances and have simplified many surgical procedures, they are not free of difficulties. For example, although it is preferable that the devices be as light and easily manipulable as possible, the couplers tend to be relatively bulky and cumbersome. This presents some difficulty, particularly with smaller diameter, relatively fragile endoscopes which, in some instances, may be as slender as two millimeters diameter. Such a slender endoscope may be damaged, such as by bending, from the weight of a comparatively heavy coupler. Additionally, the awkward, bulky type of coupler which has typified the prior art does not provide the surgeon with as comfortable and sensitive a feel as he might have if the instrument were lighter and less awkward to manipulate.

Also among the difficulties presented with the prior couplers is that they often entrap liquid or water and tend to fog up during the surgical procedure. The liquid tends to become entrapped during the sterilization procedure which, typically, requires total immersion of the endoscope, coupler and video camera, as a connected unit, in a bath of sterilization liquid such as a gluteraldehyde based solution. It is common, with the prior coupling devices for some of the liquid, even in minute quantities, to seep in between the eyepiece and the coupler, ultimately resulting in fogged up optics. Often the fogging does not begin to appear until the surgical procedure is well underway.

Another common difficulty with the prior devices is that the coupling ring which grips and engages the endoscope eyepiece does not do so in a manner which permits a smooth and steady feel when the endoscope is rotated relative to the coupler. Often the coupling rings tend to bind up or present varied resistance during rotation.

SUMMARY OF THE INVENTION

The present invention relates to a coupler for mounting a rigid endoscope and connecting it to a video camera in a manner which eliminates the conventional endoscope eyepiece. The present coupler is of a substantially reduced bulk, weight and profile. It is connectable to an endoscope, the eyepiece of which has been removed and, therefore, the coupler is free of the bulky coupling ring which has typified the prior devices. The coupler has a front section and a rear section which are rotatably connected to each other for relative rotation about a common axis. Liquid-proof seals are provided between the front and rear sections. The distal end of the front section receives the proximal end of the endoscope, but with the eyepiece removed. A special adapter and seal configuration is provided between the coupler and endoscope. The proximal end of the coupler has a connection for attachment to the video camera, also with liquid seals.

The seals between the front and rear sections also provide a smooth, steady frictional drag which enables rotation of the front and rear sections in unison or with respect to each other. When rotated, the orientation of the endoscope can be changed with respect to the camera and with respect to the field of view. All the seals are liquid-proof to enable the entire assembled unit to be sterilized by complete immersion in a sterilizing solution but without fogging the optics.

A modified embodiment of the invention is provided with a quickly detachable connection by which endoscopes may be changed quickly and easily. That feature of the invention utilizes an adapter ring which is attachable to the proximal end of the endoscope. Each endoscope to be used in the procedure is fitted with an adapter ring. The adapter ring fits within a receptive socket at the distal end of the coupler and is provided with a quickly releasable bayonet-detent connector.

It is among the objects of the invention to provide a smaller lightweight endoscope-to-video camera coupler for use in delicate surgical procedures which provides good balance and feel for the surgeon.

Another object of the invention is to provide a coupler for an endoscope and video camera which is less bulky and is easier to manipulate than prior devices.

A further object of the invention is to provide an endoscope-video camera coupler which is fully sealed to enable an entire assembly of endoscope, coupler and camera to be sterilized quickly in a liquid immersion procedure while assuring that the optics will not become fogged due to entrapment of minor quantities of liquid.

Another object of the invention is to provide an improved endoscope-video camera coupler which enables the endoscope and camera to be rotated in unison or with respect to each other to enable selective orientation between the field of view, endoscope and camera.

Still another object of the invention is to provide an improved coupler which facilitates interchanging of endoscopes during the surgical procedure.

DESCRIPTION OF THE DRAWINGS

The foregoing and other objects and advantages of the invention will be appreciated more fully from the following further description thereof, with reference to the accompanying drawings wherein:

FIG. 1 is a side elevation of a typical prior art endoscope (shown with distal tip broken away), coupler and video camera separated but in generally aligned configuration for clarity of illustration;

FIG. 1A is an illustration of the distal tip of a typical endoscope;

FIG. 2 is a side elevation of the coupler of the present invention in conjunction with a modified endoscope for use with the present invention with a video monitor, illustrated in separated configuration for clarity of illustration;

FIG. 4 is a side elevation, in section, of a modified embodiment of the coupler; and FIG. 5 is a sectional illustration along the line 5—5 of FIG. 4.

DESCRIPTION OF THE PREFERRED EMBODIMENT

Figure 3:
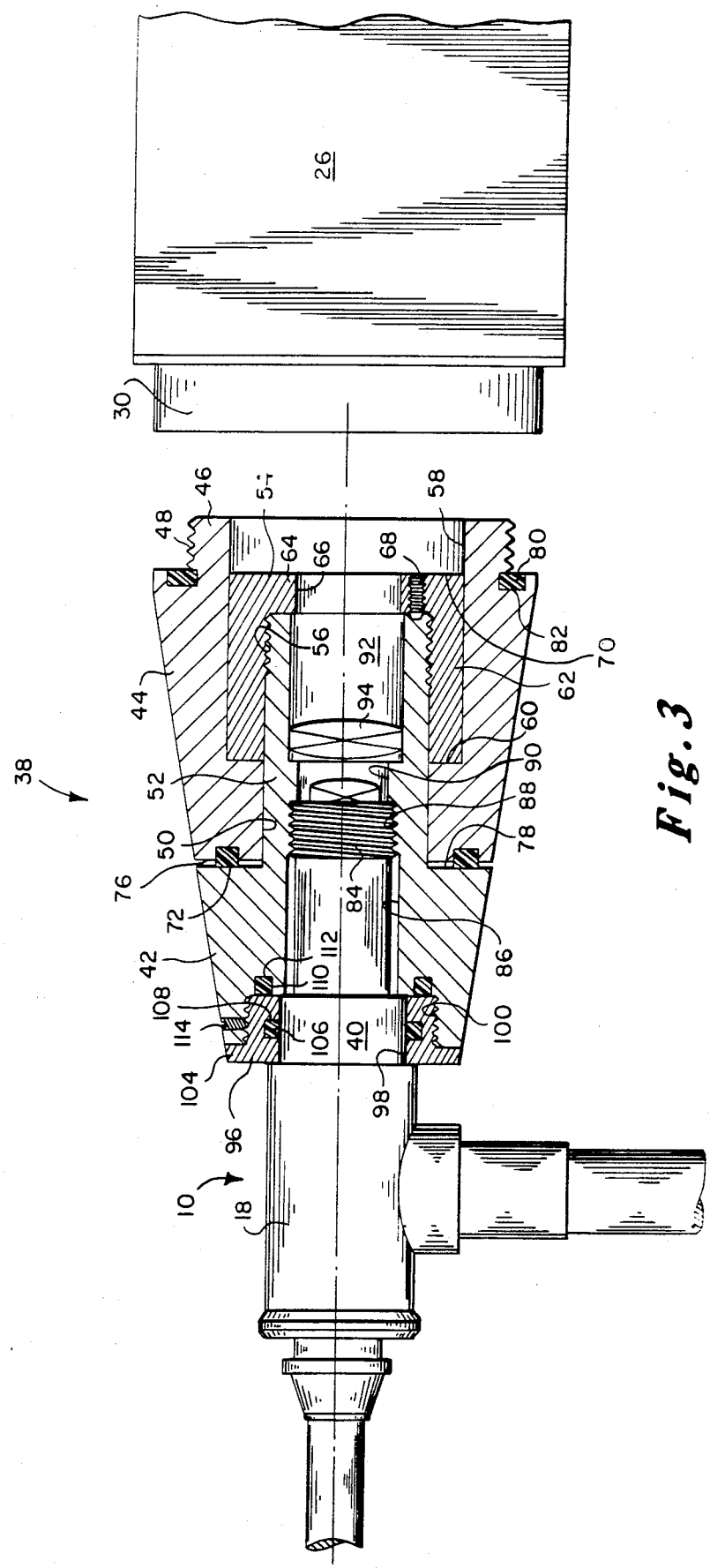
FIG. 3 is a side elevation, in section, of the endoscope, coupler and video camera of the present invention in assembled, coupled configuration.

FIG. 1 illustrates an endoscope-coupler-video camera typical of the prior art. The endoscope, indicated generally at 10, has a proximal end 12 and a distal end 14. It includes an elongate rigid tube 16 which houses a coaxial illumination and optical viewing system. The endoscope has a hub 18 near its proximal end. The hub 18 connects to an optical fiber cable 20 by which illuminating light is transmitted to the optical fibers extending through the tube 16. The viewing optics, including a number of internal lenses, extend from an objective lens 21 at the distal tip of the tube 16 (see FIG. 1A), centrally through the tube to the proximal end 12. Typically, eyepiece 22 is attached to the hub 18 at the proximal end of the endoscope 10. The eyepiece 22 conventionally has an enlarged flange at its proximal end which serves to facilitate direct visual, manual use of the endoscope by the surgeon.

As described, there is an increasing tendency to make observations with a video camera rather than directly visually. To that end it has become the practice to connect a video camera to the eyepiece 22 so that the image may be viewed and substantially magnified on a video monitor. In order to maintain the endoscopic assembly as lightweight and with the least bulk practical, the components of the video camera may be made in separate sections so that only those elements of the camera which are necessary for transducing the optical image to a video signal are actually connected to the endoscope. As shown in FIG. 1, such a video camera transducer is indicated at 26. The transducer 26 has a signal cable 28 which connects the transducer 26 to the remaining components of the camera. The front end of the transducer may have a conventional "C-mount" which consists of a distally projecting circular wall 30 with internal threads.

The endoscope 10 and video transducer 26 are connected by a coupler, indicated generally at 32. The coupler 32 typically is threaded at its proximal end, as at 34 to connect with the C-mount 30 on the video transducer 26. The distal end of the transducer 26 is detachably connectable to the eyepiece 22 of the endoscope 10. Typically the coupler 32 is provided with an enlarged coupling ring 36 which can be manipulated between an open configuration in which it will receive the flange 24 of the eyepiece 22 and a closed configuration in which it grips the eyepiece firmly. The coupler 32 also may include various internal optical lenses intended to assure that the image from the endoscope will be focused properly on the focal plane in the video transducer 36.

In order to enable the endoscope to be rotated with respect to the video transducer 26, the prior art couplers, such as coupler 32, have utilized a latch mechanism in the coupling ring 36 which enables the flange 24 of eyepiece 22 and, therefore, the endoscope, to be rotated with respect to the coupler 32. Additionally the latching mechanism grips the eyepiece flange 24 sufficiently that it takes a definite force to impart relative rotation between the endoscope 10 and video transducer 26. For example, such devices may include an arrangement of radially extending fingers which can retract radially outwardly to receive the flange 24 of eyepiece 22 and then return to a radially inwardly extending position in which they grip the flange 24 and the eyepiece 22. The gripping force is intended to be great enough so that the entire unit of endoscope 10, coupler 32 and video transducer 26 can be rotated as a unit from the proximal end of the assembly simply by manipulating the video transducer 26 or, alternately, by maintaining the video transducer 26 in a fixed position and rotating the endoscope 10. Such relative rotation enables the surgeon to view different portions of the interior of the patient's body by redirecting the orientation of the endoscope and also permits the surgeon to rearrange the attitude of the image on the video monitor.

The foregoing prior art arrangement presents a number of difficulties. The coupler 32 often has a greater bulk and heaviness than is desirable. The retaining latch mechanisms to detachably couple the eyepiece 22 from the coupler 32 do not grip the eyepiece 22 in a manner which promotes smooth rotational feel for the surgeon. Often the mechanism for detachably gripping the flange 24 does so in a manner which presents variable resistance so that the relative rotation between the eyepiece 22 and coupler 32 is not smooth but, instead, tends to bind up.

Still another significant difficulty with the foregoing type of device results from the type of sterilization commonly employed for such systems. Because the devices are intended to be used as an integral unit in the operating room they are sterilized as a coupled unit. It is necessary to sterilize simultaneously the endoscope, its cable 20, the coupler 32, the video camera 26 and the major portion of the video cable 28, all of which will be in close proximity to the surgical field. A common technique for sterilizing the assembly is to immerse it in its entirety into a bath of sterilization liquid, such as a gluteraldehyde solution. It is important that no liquid or moisture be permitted to seep into any of the components or between the connections between the coupler 32, endoscope 10 and video transducer 26. Any quantity of moisture which seeps in significantly increases the chance that the optics will become fogged at some time during the surgical procedure thereby interfering with and delaying the procedure. Among the most common locations for such leakage to occur is between the connection between the coupler 32 and the eyepiece 22 of the endoscope 10. It is among the primary objects of the present invention to avoid these and other difficulties.

FIG. 2 illustrates one embodiment of the invention and includes the endoscope 10, the video transducer 26 and the coupler 38. In accordance with the present invention the endoscope 10 is modified by removing the bulky eyepiece 22. The proximal end of the endoscope includes a slender collar 40. The barrel is receivable through the distal end of the coupler 38. The proximal end of the coupler 38 is provided with a threaded mount compatible with the C-mount of the video transducer 26. The coupler 38 is provided with front and rear sections 42, 44 at its distal and proximal ends, respectively. The front and rear sections 42, 44 are connected for relative rotation to enable relative manipulation of the endoscope 10 and video transducer 26. As can be seen in FIGS. 2 and 3 the device is of more slender, less bulky construction and is lighter than the typical prior art device. Additionally, special liquid-proof seals are provided between all components to assure that the optics will not become fogged, as described more fully below.

As shown in FIG. 3 the rear section 44 of the coupler 38 is provided with a rearwardly extending portion 46, threaded at 48, so that it can be secured to the standard C-mount of the video transducer 26. The rear section 44 is secured firmly to the video transducer 26. The rear section has a front bore 50 which receives the rearwardly extending stem 52 of the front section 42. The outer surface of the stem 52 preferably is machined to a close tolerance to the surface of the front bore 50 and facilitates smooth relative rotation between the front and rear sections 42, 44.

The front section 42 is secured rotatably to the rear section 44 by a retaining ring 54 which is secured onto the rearwardly extending portion of the stem 52, as by threads 56. The retaining ring 54 is received in a rear bore 58, which is greater in diameter than the front bore 50 of the rear section 44. The transition between the front bore 50 and rear bore 58 is defined at a shoulder 60. The retaining ring 54 includes cylindrical sidewall 62 and a rear flange 64. An aperture 66 is formed in the rear flange 64 to enable passage of the light through the coupler to the video transducer 26, as will be described further below. Once the retaining ring 54 has been screwed onto the rear end of the stem 52 to the desired extent (as will be described) it is secured in place by an appropriate means such as a set screw 68 which, in this embodiment, may bear against the rearwardly facing edge of the stem 52. The outer surface of the stem wall 62 preferably is machined to a close tolerance with respect to its mating surface 58 of the rear bore of the rear section 44. The front edge 70 of the cylindrical sidewall 62 of the retaining ring 54 also mates against the shoulder 60 of rear section 44 in a close smooth fit. The closely toleranced fit between the mating surfaces of the barrel 52 and retaining ring 54 with the bores 50, 58 and shoulder 60 also provides for a smooth rotation between the front and rear sections 42, 44.

The connection between the front and rear sections 42, 44 of the coupler 38 is sealed securely against liquid penetration by an O-ring 72. The O-ring 72 may be captured within a circular groove formed in the front face 76 of rear section 44. The O-ring 72 bears against the rearward face 78 of the front section 42. The degree to which O-ring 72 is compressed is dependent on the extent to which retaining ring 54 is screwed onto the barrel 52 of the front section 42. As retaining ring 54 is tightened the O-ring 72 is placed under an increased compressive load. This serves to both control the degree and integrity of the liquid seal as well as to vary the frictional drag between the front and rear sections 42, 44. The latter feature provides means by which the rotational feel may be adjusted within delicate limits.

An O-ring seal 80 is provided between rear section 44 and the video transducer 26. As shown, the rear O-ring is retained within a circular groove 82 so that it can face rearwardly and bear against the front facing edge of the circular wall 30 of the C-mount on the video transducer 26. Preferably the groove 82 is located so that it intersects the diameter of the threads 48, as shown. This locates the O-ring in intersecting relation to the mating threads 48 of the coupler 38 and of the threads on the wall 30 of the transducer 26. The O-ring 80, when viewed axially, intersects and overlaps the juncture of the mated threads.

The endoscope 10 is detachably connected to the front section 42 of the coupler 38. As illustrated in further detail in FIG. 3 the endoscope 10, with its eyepiece 22 removed, has a rearwardly extending barrel which is threaded at its rearwardmost end, as indicated at 84. Typically the barrel 84 will be of a smaller diameter than the hub 18 of the endoscope. The collar 40 of the endoscope is received in a socket 86 which is formed axially through the front section 42 of the coupler 38. The rearwardmost end of the socket is threaded, as at 88, to receive the threaded end 84 of the barrel. The extent to which the endoscope may be threaded into the front section may be limited by a land 90 which projects slightly radially inwardly from the socket 86 to provide an internal stop for the inner end of the collar 40. The location of the stop also is of importance in providing a reference location for the endoscope to assure that the endoscope will be optically focused on the focal plane of the video transducer 26. In that regard, the rear portion of the stem of the front section 42 may define an optical correction chamber 92 in which lenses 94 may be mounted. Such lenses, when used, are for the purpose of focusing the optical image onto the focal plane of the transducer 26. Typically such lenses will be selected with respect to the particular optical characteristics of the manufacturer's endoscopes to provide a desired optical result.

The endoscope 10 also is connected to the distal end of the front section 42 by an adapter ring 96. The adapter ring is generally cylindrical having an inner circular opening 98 which receives the collar 40 of the endoscope. The adapter ring 96 is received within an enlarged internally threaded socket 100 formed at the forward end of the front section 42. The ring 96 is securely threaded into the socket 100. The adapter ring 96 preferably has a flange at 104 at its forwardmost end. Seals are provided between the front cap 96 and each of the endoscope collar 40 and the front section 42. To that end an O-ring 106 forms a seal between the adapter ring 96 and the collar 40 of the endoscope. The O-ring is retained within a circular groove 108 formed along the inwardly facing surface of the circular opening 98. Another O-ring 110 is seated within a circular groove 112 formed in the forwardly facing surface 112 of the front section 42. When the adapter ring 96 is screwed firmly into place in the socket 100 the rearward face of the front cap engages and compresses the O-ring 110 to form a liquid-proof seal. The adapter ring may be secured to the front section 42 by a set screw 114. A number of endoscopes to be used in the procedure may be prefitted with adapter rings 96 to facilitate ready interchangability of endoscopes during a procedure.

FIG. 4 illustrates a modified embodiment of the invention utilizing a quick-detachable adapter ring as well as a modified arrangement of seals and connectors. In this embodiment the coupler includes a front section 42' and a rear section 44'. The front section 42' similarly has a rearwardly extending stem 52' which extends rearwardly through a front bore 50' formed in the rear section 44'. The front section 42' and rear section 44' are retained together by a retaining ring 120 which is threaded onto the rear portion of the stem 52' in a manner similar to retaining ring 54 of the first described embodiment. The retaining ring 120 in this embodiment is not provided with a flange at its rear end. The retaining ring 120 is secured to the stem 52' by a radially extending set screw 122 which can be accessed through radial opening 124 formed in stem 52'. As with the previous embodiment, the stem 52' may be provided with a lens chamber 92' into which appropriate lenses 94' may be mounted and secured. In this embodiment the lenses 94' may be secured by adhesive which can be applied, during assembly, through an opening 126 formed radially in the stem 52'.

The sealing arrangement between the front and rear sections 42', 44' is modified in that the seal is effected between the stem 52' and the front bore 50' of rear section 44. As shown, the stem 52' is provided with an O-ring slot 128 formed circumferentially about the stem 52' which receives an O-ring 130. The O-ring 130 effects a secure watertight seal against the bore surface 50' while also providing a smooth and constant frictional drag between the front and rear sections 42', 44'.

FIG. 4 also illustrates a quick-detachable adapter ring indicated generally at 132. The adapter ring 132 includes a cylindrical main body 134 which is slidably and rotatably received within a bore 136 formed at the distal end of the front section 42'. The rearwardly facing surface 138 of adapter ring 132 bears against a front shoulder 140 which forms and defines the bottom of bore 136. The endoscope 10 is secured, by a threaded portion 84' to the threaded axial bore 142 formed through the adapter ring 132. The adapter ring also is provided with a counterbore 144 at its distal end. A liquid-proof seal between the endoscope and adapter ring 132 is defined by an O-ring 146 which is captured within a peripheral groove 148 formed within the counterbore 144 of the adapter ring 132. The O-ring 146 seals against a portion of the endoscope, proximal of the hub, as shown.

The adapter ring 132 is quickly and easily connected to or detached from the front section 42' by a bayonet and detent arrangement shown more clearly in FIGS. 4 and 5. As shown, the adapter ring 132 is formed to include a finger 150 which extends radially from the main body 134 of the adapter ring. The finger 150 is received within a keyway formed in the bore 136 of the front section 42'. The keyway includes two segments, including a longitudinally extending segment 152 and a circumferential segment 154 which extends from the most proximal end of the longitudinal keyway 152. The L-shaped key-way cooperates with the finger 150 to define a path requiring a bayonet motion to connect or disconnect the adapter ring 132 from the front section.

The adapter ring 132 is held detachably in its place by a spring detent arrangement which latches when the adapter ring and bayonet fitting have been fully connected. To that end the adapter ring is provided with a longitudinally extending socket 156 which receives a spring and ball detent, indicated generally at 158. The shoulder 140 in the front section 42' is formed with a dimple 160 which aligns with the spring ball detent 158 when the adapter ring 132 has been advanced and twisted to its fully seated position. It retains the adapter ring securely but can be overcome with a slight twist. To that end the flange portion 133 of the adapter ring 132 should be deep enough to provide an adequate grip.

A liquid seal also is provided between the adapter ring 132 and front section 42'. The seal in this embodiment preferably is an O-ring 162 which is contained within an internal circumferential groove 164 formed within the bore 136 of front section 42', preferably rearwardly (proximally) of the finger 150 and keyway segment 154.

In each embodiment, the outer surface of the coupler section preferably defines substantially a continuous geometric surface such as the tapered cone-shape illustrated. That provides a smooth, uninterrupted feel for the surgeon while providing a gradual transition from the camera module to the endoscope.

Thus, it will be appreciated that the foregoing system avoids a number of difficulties presented with the prior devices. The entire system is moisture proof and does not fog up even after immersion in liquid sterilization baths. The weight and feel of the device is far less bulky than the prior devices. Moreover the rotational feel is smooth and does not bind up. It should be understood, however, that the foregoing description of the invention is intended merely to be illustrative thereof and that other embodiments and modifications may be apparent to those skilled in the art without departing from its spirit.

Having thus described the invention what we desire to claim and secure by Letters Patent is:

1. A coupled endoscope and video camera comprising:
   an endoscope;
   video camera means;
   coupler means for connecting the endoscope to the camera, said coupler means further comprising:
   a front coupler section and a rear coupler section, the proximal end of the endoscope being received in the front coupler section;
   first seal means for effecting a liquid seal between the endoscope and the front section;
   a rear coupler section having a rear end secured to said video camera means in liquid sealed relation;
   said front and rear coupler sections being aligned along common axis, said front section being rotatable about said axis with respect to the rear section, whereby the front section and the endoscope can be rotatably oriented with respect to the video camera means; and
   second liquid seal means between the front and rear sections.

2. A coupled endoscope and video camera as defined in claim 1 wherein the endoscope is detachably connectable to the front section of the coupler means.

3. A coupled endoscope and video camera as defined in claim 1 further comprising means for applying a frictional drag on the rotation between the front and rear sections of the coupler means.

4. A coupled endoscope and video camera as defined in claim 1 wherein the proximal end of the endoscope has a threaded portion and wherein the coupler means further comprises:
   the front section of the coupler having a threaded portion along the socket which is receptive to the threads on the proximal end of the endoscope thereby to secure the endoscope to the front section of the coupler means.

5. A coupled endoscope and video camera as defined in claim 1 further comprising:
   the front section having a rearwardly projecting stem extending along the common axis;
   the rear section having a central bore extending along the common axis, said stem being received rotatably within said bore;
   a retaining member secured to the rearward end of the stem, said retaining member being engagable with the rear coupler section as to retain the front and rear sections together while permitting relative rotation therebetween;
   the retaining member having an aperture disposed about the common axis of the coupling device to enable light to pass from said endoscope, through said stem and retaining member toward the video camera module.

6. A coupled endoscope and video camera as defined in claim 5 further comprising:
   each of said front and rear coupler sections having at least one facing surface formed on each, said facing surfaces being disposed in close facing proximity to each other and lying along planes which are non-parallel to the common axis, said facing surfaces being so located that relative axial movement between the front and rear sections will cause the space between said facing surfaces to be varied;
   said second sealing means comprising a sealing member interposed between said facing surfaces, said sealing member being adapted to be compressed between said facing surfaces;
   means for adjusting the longitudinal position of the front section with respect to this rear section so as to compress the seal between said facing surfaces.

7. A coupled endoscope and video camera as defined in claim 6 where in said second seal is constructed and arranged as to provide a dual function of a liquid seal and a frictional dragging force applying a drag to relative rotation between the front and rear sections.

8. A coupled endoscope and video camera as defined in claim 6 wherein the means for adjustably positioning the stem lengthwise of the rear section comprises:
   said retaining member being threadably connected to the stem, the retaining member being rotatably received within a bore in the rear section, the retaining member and stem being constructed and arranged so that the extent to which the retaining member is threaded onto the stem may vary the spacing between said facing surfaces and, thereby, adjust the longitudinal position of the stem and front section with respect to the rear section of the coupler means.

9. A coupled endoscope and video camera as defined in claim 8 further comprising:
   said rear section having an enlarged counterbore at its rearward end, the counterbore terminating in a shoulder at the forward end of the counterbore;
   said retaining member being rotatably received within the counterbore and being constructed so that the retaining member may engage the shoulder;
   means for securing the retaining member to the stem in a selected position with respect to the stem.

10. A coupled endoscope and video camera as defined in claim 5 wherein the front section further comprises:
    means defining a lens chamber within the stem, the lens chamber being adapted to receive corrective lenses adapted to optically couple and focus light from the endoscope onto the focal plane of the camera module.

11. A coupled endoscope and video camera as defined in claim 5 wherein the front section further comprises:
    means defining a socket extending along the central axis of the front section and into the stem portion thereof;
    an inner region of the socket being threaded to receive a threaded proximal end of the barrel of the endoscope;
    means defining a stop along said socket to engage and limit the position of the endoscope axially with respect to the front section.

12. A coupled endoscope and video camera as defined in claim 2 wherein the endoscope is detachably connectable to the front section of the coupler means by means comprising:
    an adapter having an opening therethrough to receive the proximal end of the endoscope;

means for detachably securing the adapter to the front coupler section;

said first seal means comprising means for effecting a seal between the endoscope and the adapter and for defining a seal between the adapter and the front coupler section.

13. A coupled endoscope and video camera as defined in claim 12 wherein the means for detachably connecting the adapter to the front coupler section comprises a bayonet connection between the adapter and front section and detent means for detachably latching the adapter in a fully connected position.

14. A coupled endoscope and video camera as defined in claim 12 wherein the proximal end of the endoscope has a threaded portion and wherein the coupler means further comprises:

the adapter having a threaded portion which is receptive to the threads on the proximal end of the endoscope thereby to secure the endoscope to the adapter.

15. A coupled endoscope and video camera as defined in claim 3 wherein the means for applying a frictional drag comprises said second liquid seal means.

16. A coupled endoscope and video camera as defined in claim 5 further comprising:

means defining a seal between the stem of said front section and the central bore of said rear section.

17. A coupled endoscope and video camera as defined in claim 1 wherein the front and rear sections are contoured externally to define a substantially continuous geometric surface.

18. A coupled endoscope and video camera as defined in claim 17 wherein said geometric surface tapers from the proximal to the distal end of the coupler means.

* * * * *